(12) United States Patent
Goettel et al.

(10) Patent No.: US 7,195,649 B2
(45) Date of Patent: Mar. 27, 2007

(54) N-ARYL-4,5-DIAMINOPYRAZOLES AND DYES CONTAINING SAID COMPOUNDS

(75) Inventors: Otto Goettel, Marly (CH); Wolfram Geibel, Huenfeld (DE); Emmanuel Morand, Neyruz (CH)

(73) Assignee: Wella AG, Darmstadt (DE)

( * ) Notice: Subject to any disclaimer, the term of this patent is extended or adjusted under 35 U.S.C. 154(b) by 324 days.

(21) Appl. No.: 10/501,151

(22) PCT Filed: May 14, 2003

(86) PCT No.: PCT/EP03/05031

§ 371 (c)(1),
(2), (4) Date: Jul. 12, 2004

(87) PCT Pub. No.: WO2004/047781

PCT Pub. Date: Jun. 10, 2004

(65) Prior Publication Data
US 2005/0081312 A1  Apr. 21, 2005

(30) Foreign Application Priority Data
Nov. 22, 2002 (DE) .......................... 102-54-506

(51) Int. Cl.
*A61K 7/13* (2006.01)
(52) U.S. Cl. .................. 8/405; 8/406; 8/409; 8/410; 8/421; 8/423; 8/568; 548/365.7
(58) Field of Classification Search .................. 8/405, 8/406, 409, 410, 421, 423, 568; 548/365.7
See application file for complete search history.

(56) References Cited

U.S. PATENT DOCUMENTS

| 5,061,289 | A  | 10/1991 | Clausen et al. |
| 2001/0009044 | A1* | 7/2001 | Braun ............................ 8/405 |
| 2002/0050013 | A1 | 5/2002 | Burande |
| 2003/0131423 | A1 | 7/2003 | Javet et al. |
| 2004/0255397 | A1 | 12/2004 | Fessmann et al. |

FOREIGN PATENT DOCUMENTS

| DE | 200 13 156 | 11/2000 |
| DE | 101 09 806 A1 | 9/2002 |
| EP | 0 375 977 A1 | 7/1990 |
| WO | 03 008405 A | 1/2003 |

* cited by examiner

*Primary Examiner*—Eisa Elhilo
(74) *Attorney, Agent, or Firm*—Michael J. Striker

(57) ABSTRACT

N-Aryl-4,5-diaminopyrazole of formula (I) or a physiologically compatible salt thereof of an organic or inorganic acid

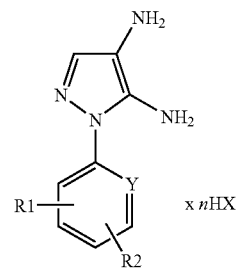

(I)

wherein
R1 and R2 independently of each other denote a hydrogen atom, a straight-chain or branched $C_1$–$C_6$-alkyl group, a hydroxyl group, a straight-chain or branched $C_1$–$C_6$-monohydroxyalkyl group, a straight-chain or branched $C_3$–$C_6$-dihydroxyalkyl group, a straight-chain or branched $C_1$–$C_6$-alkoxy group, a straight-chain or branched $C_1$–$C_6$-hydroxyalkoxy group, a straight-chain or branched $C_3$–$C_6$-dihydroxyalkoxy group, an amino group, a $C_1$–$C_4$-monoalkylamino group, a di($C_1$–$C_4$)-alkylamino group, a halogen atom, a difluoromethyl group or a trifluoromethyl group; Y stands for a nitrogen atom or a C-R3 group, wherein C is a carbon atom of the aromatic ring and R3 is a hydrogen atom, a halogen atom, a straight-chain or branched $C_1$–$C_6$-alkyl group, a straight-chain or branched $C_1$–$C_6$-hydroxyalkyl group, a straight-chain or branched $C_1$–$C_6$-alkoxy group, a straight-chain or branched $C_2$–$C_6$-hydroxyalkoxy group or a straight-chain or branched $C_2$–$C_6$-alkoxyalkoxy group; X denotes an acid radical and n has a value from 0 to 3; provided that when Y stands for a C-R3 group, at least one of the R1, R2 and R3 groups is different from hydrogen; as well as colorants for keratin fibers containing these compounds.

10 Claims, No Drawings

N-ARYL-4,5-DIAMINOPYRAZOLES AND DYES CONTAINING SAID COMPOUNDS

CROSS-REFERENCE

This is the U.S. National Stage of PCT/EP 03/05031, filed on May 14, 2003 (International filing date), which claims the benefit of priority of invention under 35 U.S.C. 119 and 365 (b) based on DE 102 54 506.5 filed Nov., 22, 2002 in Germany.

BACKGROUND OF THE INVENTION

The present patent application has for an object new, aryl-substituted 4,5-diaminopyrazoles and colorants for keratin fibers containing these compounds.

In the area of keratin fiber dyeing, particularly hair dyeing, oxidation dyes have attained substantial importance. In this case, the coloration is produced by reaction of certain developers with certain couplers in the presence of an appropriate oxidant. Now as before, hair colorants for dyeing in the natural color shade range are particularly important. In addition, by combination of suitable oxidation dye precursors, it is also possible to produce currently fashionable color shades. Currently popular are modified natural shades, for example brown shades with pronounced eggplant or copper tones and particularly brilliant red tones.

In addition to being able to produce color effects, oxidation dyes intended for use in treating human hair must meet many other requirements. Such dyes must be unobjectionable from a toxicological and dermatological standpoint, and the colorations achieved must show good light fastness, resistance to permanent waving, rubbing fastness, resistance to shampooing and sufficient resistance to perspiration. Moreover, by combination of suitable developers and couplers it must be possible to produce a wide range of different color shades.

In the past, the red range, which as before is important, was provided predominantly by use of 4-aminophenol as the developer. Because of concerns about the physiological compatibility of this substance, derivatives of pyridine and pyrimidine have also been used, but they were unsatisfactory from a coloring standpoint. A significant improvement in color stability in the red range was achieved for the first time by replacing p-aminophenol with 4,5-diaminopyrazoles described in EP-A 0 375 977. Moreover, DE-A 101 09 806 discloses combinations of substituted pyrazolones and 4,5-diaminopyrazoles to create yellow to orange shades.

Whereas most oxidation dyes hardly show any weaknesses on undamaged hair, major differences can arise on damaged hair. Hence, the hairdresser knows from his everyday practice the problem that dyes are not absorbed uniformly by the hair to be dyed. Whereas the hair roots are usually intact, the hair tips in the course of time show damage caused by the effect of weather factors and frequent washing and combing and which increases from the roots to the tips of the hair. When such hair is dyed, then because of the nonuniform hair structure between roots and tips, the coloring results can be nonuniform. Another problem lies in that during washing the dyes are more strongly washed out from the damaged hair regions than from the undamaged ones, which after a few hair washings can become gradually more noticeable depending on the degree of hair damage. In particular, the customer also notices this because the hair tips look dull.

SUMMARY OF THE INVENTION

A need thus continued to exist for dyes that, on the one hand, would give highly brilliant color shades and, on the other, have markedly improved color resistance to shampooing on hair varying greatly in quality, particularly on hair damaged by permanent waving or bleaching. Moreover, the color shades produced should not loose their brilliance even after several hair washings.

We have now found that the N-aryl-4,5-diaminopyrazoles of formula (I) described in the following meet the aforesaid requirements in outstanding manner in that besides heretofore unequaled color brilliance and color depth these new dyes provide markedly improved color stability.

The present invention therefore has for an object N-aryl-4,5-diaminopyrazoles of formula (I) or their physiologically compatible salts of organic or inorganic acids

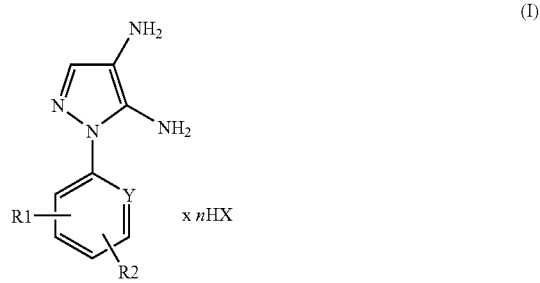

wherein

R1 and R2 independently of each other denote a hydrogen atom, a straight-chain or branched $C_1$–$C_6$-alkyl group, a hydroxyl group, a straight-chain or branched $C_1$–$C_6$-monohydroxyalkyl group, a straight-chain or branched $C_3$–$C_6$-dihydroxyalkyl group, a straight-chain or branched $C_1$–$C_6$-alkoxy group, a straight-chain or branched $C_1$–$C_6$-hydroxyalkoxy group, a straight-chain or branched $C_3$–$C_6$-dihydroxyalkoxy group, an amino group, a $C_1$–$C_4$-monoalkylamino group, a di($C_1$–$C_4$)-alkylamino group, a $C_1$–$C_4$-aminoalkyl group, a halogen atom (F, Cl, Br, I), a difluoromethyl group or a trifluoromethyl group;

Y stands for a nitrogen atom, or a C-R3 group, wherein C is a carbon atom of the aromatic ring and R3 is a hydrogen atom, a halogen atom (F, Cl, Br, I), a straight-chain or branched $C_1$–$C_6$-alkyl group, a straight-chain or branched $C_1$–$C_6$-hydroxyalkyl group, a straight-chain or branched $C_1$–$C_6$-alkoxy group, a straight-chain or branched $C_2$–$C_6$-hydroxyalkoxy group or a straight-chain or branched $C_2$–$C_6$-alkoxyalkoxy group;

X denotes an acid radical and n has a value from 0 to 3; provided that when Y stands for a C-R3 group, at least one of the R1, R2 and R3 groups is different from hydrogen.

Preferred compounds of formula (I) are those wherein:

R1 and R2 independently of each other denote hydrogen, a methyl group, an ethyl group, an isopropyl group, an amino group or a methoxy group; and Y stands for a C—H group, a C—Cl group, a C-methyl group or a C-ethyl group and, in particular, a nitrogen atom, and when Y stands for a C—H group at least one of the R1 and R2 groups is not hydrogen.

Particularly preferred are the following compounds of formula (I):

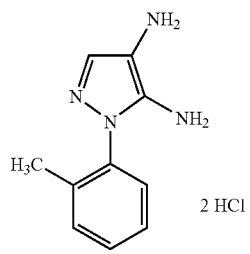

1-(2-methylphenyl)-4,5-diamino-1H-pyrazole dihydrochloride (I-a)

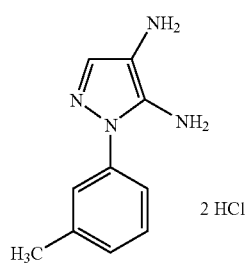

1-(3-methylphenyl)-4,5-diamino-1H-pyrazole dihydrochloride (I-b)

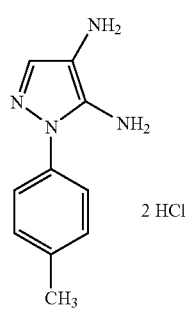

1-(4-methylphenyl)-4,5-diamino-1H-pyrazole dihydrochloride (I-c)

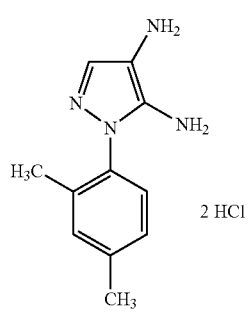

1-(2,4-dimethylphenyl)-4,5-diamino-1H-pyrazole dihydrochloride (I-d)

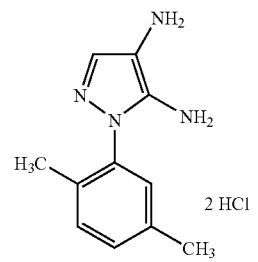

1-(2,5-dimethylphenyl)-4,5-diamino-1H-pyrazole dihydrochloride (I-e)

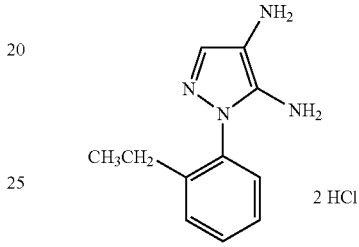

1-(2-ethylphenyl)-4,5-diamino-1H-pyrazole dihydrochloride (I-f)

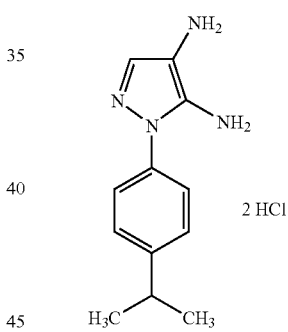

1-(4-isopropylphenyl)-4,5-diamino-1H-pyrazole dihydrochloride (I-g)

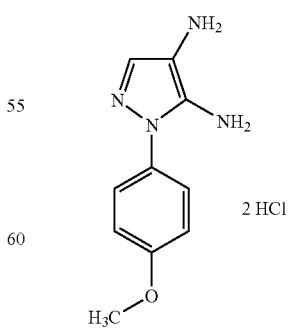

1-(4-methoxylphenyl)-4,5-diamino-1H-pyrazole dihydrochloride (I-h)

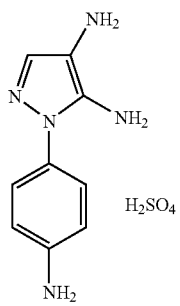

1-(4-aminophenyl)-4,5-diamino-1H-pyrazole sulfate (1:1) (I-i)

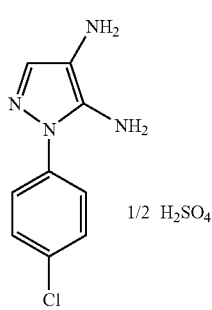

1-(4-chlorophenyl)-4,5-diamino-1H-pyrazole sulfate (2:1) (I-k)

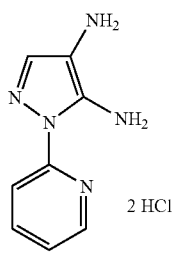

1-(2-pyridinyl)-4,5-diamino-1H-pyrazole dihydrochloride (I-l)

The compounds of formula (I) can be prepared by methods analogous to the known ones, for example by cyclization of an arylhydrazine with methoxyacrylonitrile, ethoxyacrylonitrile or chloroacrylonitrile, or else, in ideal fashion, with dimethylaminoacrylonitrile according to the general method according to Scheme 1:

Scheme 1

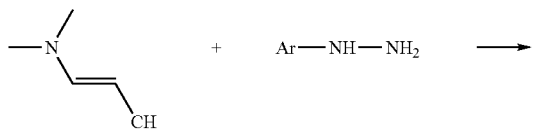

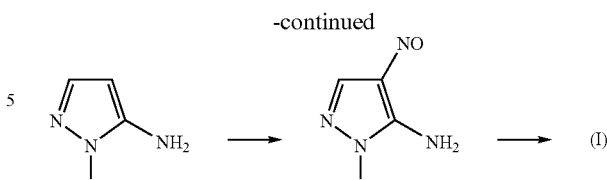

In certain cases, however, it may be advantageous from a preparative standpoint to subject the 5-aminopyrazoles to reaction with a diazonium salt, as shown in Scheme 2, to form an azo dye, then cleaving the dye and isolating the compound of formula (I).

Scheme 2

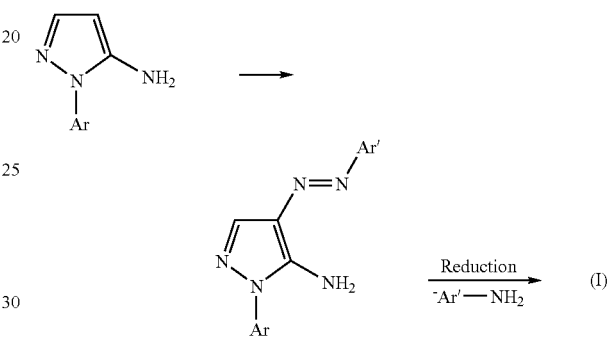

Eminently suited for the preparation of the intermediate azo compounds are aniline, anilines substituted with one or more $C_1$–$C_6$-groups or anisidines, sulfanilic acid, metanilic acid, orthanilic acid, p-aminobenzoic acid, m-aminobenzoic acid and 5-aminoisophthalic acid. Particularly preferred among these compounds are sulfanilic acid, p-aminobenzoic acid and 5-aminoisophthalic acid.

For better handling, the N-aryl-4,5-diaminopyrazoles of formula (I) of the invention are not isolated in the form of the free bases but preferably in the form of the corresponding salts which are less sensitive to oxidation. The acids used can be inorganic or organic acids, and preferably citric acid, tartaric acid, phosphoric acid and especially hydrochloric acid or sulfuric acid.

The compounds of formula (I) are eminently suited as dye precursors in the oxidative system for dyeing keratin fibers. Although these compounds are suitable particularly for use in dyeing keratin fibers, for example wool, silk or hair, particularly human hair, these compounds can in principle also be used to dye other natural or synthetic fibers, for example cotton or nylon 6,6.

Another object of the present invention is therefore a colorant for oxidative dyeing of keratin fibers, for example wool, furs, feathers or hair and particularly human hair, characterized in that it contains at least one N-aryl-4,5-diaminopyrazole of general formula (I) or a physiologically compatible salt thereof.

The colorant of the invention contains the N-aryl-4,5-diaminopyrazoles of formula (I) in an amount from about 0.005 to 20 weight percent, preferably in an amount from about 0.01 to 10 weight percent and particularly from 0.1 to 6 weight percent.

The compounds of formula (I) can be used alone or in combination with known developers and/or couplers commonly used in systems for oxidative dyeing of fibrous materials.

Suitable couplers are, in particular, N-(3-dimethylaminophenyl)urea, 2,6-diaminopyridine, 2-amino-4-[(2-hydroxyethyl)amino]anisole, 2,4-diamino-1-fluoro-5-methylbenzene, 2,4-diamino-1-methoxy-5-methyl benzene, 2,4-diamino-1-ethoxy-5-methylbenzene, 2,4-diamino-1-(2-hydroxyethoxy)-5-methyl-benzene, 2,4-di[(2-hydroxyethyl)amino]-1,5-dimethoxybenzene, 2,3-diamino-6-methoxypyridine, 3-amino-6-methoxy-2-(methylamino)pyridine, 2,6-diamino-3,5-dimethoxypyridine, 3,5-diamino-2,6-di-methoxypyridine, 1,3-diaminobenzene, 2,4-diamino-1-(2-hydroxyethoxy)benzene, 2,4-diamino-1-(3-hydroxypropoxy)benzene, 2,4-diamino-1-(3-methoxypropoxy)benzene, 1-(2-aminoethoxy)-2,4-diaminobenzene, 2-amino-1-(2-hydroxyethoxy)₄-methylaminobenzene, 2,4-diaminophenoxyacetic acid, 3-[di(2-hydroxyethyl)amino]aniline, 4-amino-2-di[(2-hydroxyethyl)amino]-1-ethoxybenzene, 5-methyl-2-(1-methylethyl)phenol, 3-[(2-hydroxyethyl)amino]aniline, 3-[(2-aminoethyl)amino]aniline, 1,3-di(2,4-di-aminophenoxy)propane, di(2,4-diaminophenoxy)methane, 1,3-di-amino-2,4-dimethoxybenzene, 2,6-bis(2-hydroxyethyl)aminotoluene, 4-hydroxyindole, 3-dimethylaminophenol, 3-diethylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methylphenol, 3-amino-2-chloro-6-methylphenol, 3-aminophenol, 2-[(3-hydroxyphenyl)amino]acetamide, 5-[(2-hydroxyethyl)amino]-2-methylphenol, 3-[(2-hydroxyethyl)amino]phenol, 3-[(2-methoxyethyl)amino]phenol, 5-amino-2-ethylphenol, 2-(4-amino-2-hydroxyphenoxy)ethanol, 5-[(3-hydroxypropyl)amino]-2-methylphenol, 3-[(2,3-dihydroxypropyl)amino]-2-methylphenol, 3-[(2-hydroxyethyl)amino]-2-methylphenol, 2-amino-3-hydroxypyridine, 5-amino-4-chloro-2-methylphenol, 1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihydroxybenzene, 1-chloro-2,4-dihydroxy-benzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methyl-benzene, 1,3-dihydroxy-2,4-dimethylbenzene, 3,4-methylenedioxyphenol, 3,4-methylenedioxyaniline, 5-[(2-hydroxyethyl)amino]-1,3-benzodioxole, 6-bromo-1-hydroxy-3,4-methylenedioxybenzene, 3,4-diaminobenzoic acid, 3,4-dihydro-6-hydroxy-1,4-(2H)-benzoxazine, 6-amino-3,4-dihydro-1,4(2H)benzoxazine, 3-methyl-1-phenyl-5-pyrazolone, 5,6-dihydroxyindole, 5,6-dihydroxyindoline, 4-hydroxyindole, 5-hydroxyindole, 6-hydroxyindole, 7-hydroxyindole and 2,3-indolinedione or the salts thereof.

To prepare the natural-like shades and fashionable red shades, it is particularly advantageous to use the compounds of formula (I) in combination with additional developers. Suitable developers are p-phenylenediamines, p-aminophenols and other 4,5-diaminopyrazoles or the salts thereof.

Particularly noteworthy are the following developers:
1,4-diaminobenzene (p-phenylenediamine), 1,4-diamino-2-methylbenzene (p-toluylene-diamine), 1,4-diamino-2,6-dimethylbenzene, 1,4-diamino-2,5-dimethylbenzene, 1,4-diamino-2,3-dimethylbenzene, 2-chloro-1,4-diaminobenzene, 4-phenylaminoaniline, 4-dimethylaminoaniline, 4-diethylaminoaniline, 4-[di(2-hydroxyethyl)amino]anine, 4-[(2-methoxyethyl)amino]aniline, 4-[(3-hydroxypropyl)amino]aniline, 1,4-diamino-2-(2-hydroxyethyl)benzene, 1,4-diamino-2-(1-hydroxyethyl)benzene, 1,4-diamino-2-(1-methylethyl)benzene, 1,4-diamino-2-(1-methylethyl)benzene, 1,3-bis[(4-aminophenyl)-(2-hydroxy-ethyl)amino]-2-propanol, 1,8-bis-(2,5-diaminophenoxy)-3,6-dioxaoctane, 4-aminophenol, 4-amino-3-methylphenol, 4-methylaminophenol, 4-amino-2-(aminomethyl)phenol, 4-amino-2-[(2-hydroxy-ethyl)amino]methylphenol, 4-amino-2-(methoxymethyl)phenol, 4-amino-2-(2-hydroxyethyl)phenol, 5-aminosalicylic acid, 2,5-diaminopyridine, 2,4,5,6-tetraminopyrimidine, 2,5,6-triamino-4-(1H)-pyrimidone, 4,5-diamino-1-(2-hydroxyethyl)-1H-pyrazole, 4,5-diamino-1-(1-methylethyl)-1H-pyrazole, 4,5-diamino-1-(4-methylbenzyl)-1H-pyrazole, 1-(4-chlorobenzyl)-4,5-diamino-1H-pyrazole, 4,5-diamino-1-methyl-1H-pyrazole, 4,5-diamino-3-methyl-1-phenyl-1H-pyrazole, 4,5-diamino-1-methyl-1H-pyrazole, 4,5-diamino-1-pentyl-1H-pyrazole, 4,5-diamino-1-benzyl-1H-pyrazole, 4,5-diamino-1-(4-methoxybenzyl)-1H-pyrazole, 4,5-diamino-1-(2-hydroxyethyl)-3-methyl-1H-pyrazole, 2-aminophenol, 2-amino-6-methylphenol and 2-amino-5-methylphenol or the salts thereof.

The aforesaid developers and couplers can be used individually or in admixture with one another, the aforesaid known developers and couplers being contained in the colorant of the invention in a total amount from about 0.01 to 20 weight percent and preferably from about 0.2 to 6 weight percent.

Moreover, the colorant of the invention can contain other dye components, for example 4-(2,5-diaminobenzylamino)aniline or 3-(2,5-diaminobenzylamino)aniline, as well as common natural dyes, dyes identical to natural ones, or synthetic direct dyes from the group consisting of anionic (acid) and cationic (basic) dyes, triarylmethane dyes, nitro dyes, disperse dyes and azo dyes, for example natural dyes such as indigo or henna, triphenylmethane dyes such as 4-[(4'-aminophenyl)-(4'-imino-2',5"-cyclohexadien-1"-ylidene)methyl]-2-methylaminobenzene monohydrochloride (C.I. 42510), and 4-[(4'-amino-3'-methylphenyl)-(4"-imino-3"-methyl-2',5"-cyclohexadien-1"-ylidene)methyl]-2-methylamino-benzene monohydrochloride (C.I. 42520), aromatic nitro dyes such as 4-(2'-hydroxyethyl)-aminonitrotoluene, 2-amino-4,6-dinitrophenol, 2-amino-5-(2'-hydroxyethyl)aminonitrobenzene, 2-chloro-6-(ethylamino)₄-nitrophenol, 4-chloro-N-(2-hydroxyethyl)-2-nitroaniline, 5-chloro-2-hydroxy-4-niroaniline, 2-amino-4-chloro-6-nitrophenol and 1-[(2'-ureidoethyl)amino-4-nitrobenzene, azo dyes such as sodium 6-[(4'-aminophenyl)azo]-5-hydroxynaphthalene-1-sulfonate (C.I. 14805) and disperse dyes, for example 1,5-diaminoanthraquinone and 1,4,5,8-tetraminoanthraquinone.

The colorant of the invention contains the direct dyes at a total concentration from about 0.1 to 10 weight percent and preferably from about 0.1 to 5 weight percent.

Naturally, the dyes, provided they are bases, can also be used in the form of their physiologically compatible salts of organic or inorganic acids, for example hydrochloric acid or sulfuric acid, or—if they contain aromatic OH— groups—in the form of salts of bases, for example as alkali metal phenoxides.

For dyeing, the abovesaid combinations of compounds of formula (I) of the invention with oxidative hair dye precursors and/or direct dyes are applied in an appropriate dye carrier composition.

Moreover, the colorants can also contain other common additives, for example antioxidants such as ascorbic acid, thioglycolic acid or sodium sulfite, as well as perfume oils, penetrants, buffering systems, complexing agents, preservatives, wetting agents, emulsifiers, thickeners and hair-care agents.

The colorant of the invention can be formulated, for example, as a solution, particularly an aqueous or aqueous-alcoholic solution, or as a paste, cream, gel, emulsion or aerosol preparation. Such a colorant preparation consists of a mixture of dye components and additives commonly used for such preparations.

Common additives to solutions, creams, emulsions or gels are, for example, solvents such as water, lower aliphatic alcohols, for example ethanol, propanol or isopropanol, glycerol or glycols such as 1,2-propylene glycol; moreover wetting agents or emulsifiers from the classes of anionic, cationic, amphoteric or nonionic surface-active substances such as, for example, the fatty alcohol sulfates, ethoxylated fatty alcohol sulfates, alkylsulfonates, alkylbenzenesulfonates, alkyltrimethylammonium salts, alkylbetaines, ethoxylated fatty alcohols, ethoxylated nonylphenols, fatty alkanolamides and ethoxylated fatty esters, furthermore thickeners such as the higher fatty alcohols, starch, cellulose derivatives, petrolatum, paraffin oil and fatty acids; moreover hair-care agents such as cationic resins, lanolin derivatives, cholesterol, pantothenic acid and betaine. The said constituents are used in amounts commonly employed for such purposes, for example the wetting agents and emulsifiers at a concentration from about 0.5 to 30 weight percent, the thickeners in an amount from about 0.1 to 30 weight percent and the hair-care agents at a concentration from about 0.1 to 5 weight percent.

Depending on the composition, the colorant of the invention can be weakly acidic, neutral or alkaline. In particular, it has a pH from 6 to 11.5, the adjustment to a basic value preferably being achieved with ammonia or an organic amine, for example monoethanolamine or triethanolamine, or an amino acid, or an inorganic base such as sodium hydroxide or potassium hydroxide. It is also possible to use combinations of the aforesaid compounds, particularly a combination of ammonia and monoethanolamine. For pH adjustment in the acidic range, an inorganic or organic acid, for example phosphoric acid, acetic acid, citric acid or tartaric acid, can be used.

For use in oxidative hair dyeing, the afore-described colorant (pH=6 to 11.5) is mixed with an oxidant (pH=2 to 6.5) just before use. The pH of the ready-for-use hair colorant depends on the amount of alkali in the dye carrier and of acid in the oxidant, as well as on the mixing ratio. Depending on the composition, the ready-for-use colorant can be weakly acidic, neutral or alkaline and have a pH from about 3 to 11 and preferably from about 5 to 10.

Suitable oxidants for developing the hair coloration are mainly hydrogen peroxide or the compounds of addition thereof to urea, melamine, sodium borate or sodium carbonate in the form of a 3 to 12%, preferably 6% aqueous solution. Atmospheric oxygen can also be used. Based on a 6% concentration of free hydrogen peroxide in the oxidant, the weight ratio of hair colorant to oxidant is from about 5:1 to 1:2 and preferably 1:1. Larger amounts of oxidant are used primarily at higher dye concentrations in the hair colorant or when more pronounced hair bleaching is wanted at the same time.

This mixture is applied to the hair in an amount sufficient for the hair treatment, in general from about 60 to 200 grams depending on the fullness of the hair, and the mixture is allowed to act on the hair at 15 to 50° C. for about 10 to 45 minutes and preferably 30 minutes, after which the hair is rinsed with water and dried. Optionally, following this rinsing the hair is washed with a shampoo and optionally post-rinsed with a weak organic acid, for example citric acid or tartaric acid. The hair is then dried.

The colorant of the invention containing an N-aryl-4,5-diaminopyrazole of formula (I) gives hair colorations of excellent color stability, particularly in terms of light fastness, wash fastness and rubbing fastness. As far as the coloring properties are concerned, depending on the kind and composition of the dye components, the colorants of the invention provide a wide range of different color shades particularly in the range of the fashionable red shades. The shades show unusual color intensity and brilliance. The very good coloring properties of the colorants of the present patent application manifest themselves particularly in that these colorants provide uniform and durable colorations even on hair previously damaged to different degrees.

The following examples will explain in greater detail the subject matter of the invention without limiting its scope.

EXAMPLES

Example 1

Preparation of 1-(4-methoxyphenyl)-4,5-diamino-1H-pyrazole dihydrochloride

Step 1.1: 5-Amino-1-(4-methoxyphenyl)-1H-pyrazole 20.43 g (117 mmol) of 4-methoxyphenylhydrazine hydrochloride and 12.5 g (130 mmol) of 3-dimethylaminoacrylonitrile in 200 mL of methanol were heated at reflux for 2 hours. The reaction mixture was allowed to cool and was then poured onto 600 mL of ice water upon which the 5-amino-1-(4-methoxyphenyl)pyrazole [sic] precipitated. Filtration and drying gave 17.4 g (92 mmol, 79% of the theoretical) of a purplish product.

$^1$H-NMR (DMSO-d$_6$): δ=3.60 ppm (d, $^4J_{HH}$=7.0 Hz, 2H); 3.67 ppm (s, 3H); 6.81 ppm (d, $^3J_{HH}$=11.0 Hz, 2H); 6.85 ppm (d, $^3J_{HH}$=11.0 Hz, 2H); 7.00 ppm (t, $^4J_{HH}$=7.0 Hz, 1H); 9.90 ppm (s, 1H).

Step 1.2: 5-Amino-1-(4-methoxyphenyl)-4-nitrosopyrazole hydrochloride 17.4 g (92 mmol) of 5-amino-1-(4-methoxyphenyl)pyrazole [sic] from Step 1.1 was dissolved in 200 mL of tetrahydrofuran, 52.4 g of 32% hydrochloric acid was added, and the mixture was cooled to 0–5° C. Then 11.8 g (101 mmol) of isopentyl nitrite was added dropwise with agitation so that the temperature did not exceed 5° C. Gradually, a brownish precipitate formed which after an additional 2-hour agitation period in an ice bath was removed by suction filtration and washed with a small amount of tetrahydrofuran. Drying gave 16.4 g (64 mmol, 70% of the theoretical) of 5-amino-1-(4-methoxyphenyl)-4-nitrosopyrazole hydrochloride.

$^1$H-NMR (DMSO-d$_6$): δ=3.83 ppm (s, 3H); 7.0 ppm (s broad, 3H); 7.11 ppm (d, $^3J_{HH}$=15 Hz, 2H; 7.45 ppm (d, $^3J_{HH}$=15 Hz, 2H); 8.75 ppm (s, 1H).

Step 1.3: 1-(4-Methoxyphenyl)-4,5-diamino-1H-pyrazole dihydrochloride 8.0 g (31 mmol) of 5-amino-1-(4-methoxyphenyl)-4-nitrosopyrazole hydrochloride from Step 1.2 in 200 mL of ethanol was hydrogenated for 6 hours on 0.8 g of Pd/C (10%) at 8 bar of hydrogen pressure. The catalyst was filtered off, and the reaction mixture was concentrated to a total volume of about 30 mL. After the addition of 40 mL of 3-molar ethanolic hydrochloric acid and agitation in an ice bath, the product crystallized. Suction filtration and washing with 50 mL of ethyl acetate gave 7.4 g (27 mmol), 86% of the theoretical) of 1-(4-methoxyphenyl)-4,5-diamino-1H-pyrazole dihydrochloride.

$^1$H-NMR (DMSO-d$_6$): δ=3.82 ppm (s, 3H; 5.29 ppm (s broad, 3H); 7.07 ppm (d, $^3$J$_{HH}$=15 Hz, 2H); 7.44 ppm (d, $^3$J$_{HH}$=15 Hz, 2H); 7.46 ppm (s, 1H); 10.04 ppm (s broad, 3H).

Example 2

Preparation of
1-(4-isopropylphenyl)-4,5-diamino-1H-pyrazole
dihydrochloride

Step 2.1: 5-Amino-1-(4 isopropylphenyl)-1H-pyrazole 15.7 g (84 mmol) of 4-isopropylphenylhydrazine hydrochloride and 8.9 g (93 mmol) of 3-dimethylaminoacrylonitrile in 150 mL were heated at reflux for 3 hours. The reaction mixture was then cooled and poured into 600 mL of ice water which caused 5-amino-1-(4-isopropylphenyl)pyrazole [sic] to precipitate. Filtering, washing with 100 mL of water and drying gave 14.9 g (74 mmol, 88% of the theoretical) of a beige product.

$^1$H-NMR (DMSO-d$_6$): δ=1.17 ppm (d, $^3$J$_{HH}$=11.3 Hz, 6H); 2.78 ppm (h, $^3$J$_{HH}$=11.3 Hz, 1H); 6.88 ppm (d, $^3$J$_{HH}$=14.1 HZ, 2H); 7.05 ppm (s, I); 7.07 ppm (d, $^3$J$_{HH}$=14.1 Hz, 2H); 10.02 ppm (s, 1H).

Step 2.2: 5-amino-1-(4-isopropylphenyl)$_4$-nitroso-1H-pyrazole hydrochloride 14.9 g (74 mmol) of 5-amino-1-(4-isopropylphenyl)pyrazole [sic] from Step 2.1 was dissolved in 130 mL of tetrahydrofuran. 42.2 g of 32% hydrochloric acid was added, and the reaction mixture was cooled to 0 to 5° C. Then, 9.5 g (81 mmol) of isopentyl nitrite was added dropwise with agitation so that the temperature did not exceed 5° C. Gradually, a yellowish precipitate formed which after an additional 1.5-hour agitation period in an ice bath was removed by suction filtration and washed with a small amount of tetrahydrofuran. Drying gave 12.3 g (46.1 mmol, 62% of the theoretical) of 5-amino-1-(4-isopropylphenyl)$_4$-nitroso-1H-pyrazole hydrochloride.

$^1$H-NMR (DMSO-d$_6$): δ=1.25 ppm (d, $^3$J$_{HH}$=11.7 Hz, 6H); 2.99 ppm (h, $^3$J$_{HH}$=11.7 Hz, 1H); 7.45 ppm (m centered, 4H); 8.77 ppm (s, 1H).

Step 2.3: 4,5-Diamino]-(4-isopropylphenyl)-1H-pyrazole dihydrochloride 6.0 g (22.5 mmol) of 5-amino-1-(4-isopropylphenyl)-4-nitroso-1H-pyrazole hydrochloride from Step 2.2 in 150 mL of ethanol was hydrogenated for 6 hours on 0.6 g of Pd/C (10%) at 8 bar of hydrogen pressure. The catalyst was filtered off, and the filtrate was concentrated to a total volume of about 20 mL. After the addition of 40 mL of a 3-molar ethanolic hydrochloric acid solution and agitation in an ice bath, the product crystallized out. Suction filtration and washing with 50 mL of ethyl acetate gave 5 g (17.2 mmol, 77% of the theoretical) of 4,5-diamino-1-(4-isopropylphenyl)-1H-pyrazole dihydrochloride as a colorless product.

$^1$H-NMR (DMSO-d$_6$): δ=1.24 ppm (d, $^3$J$_{HH}$=11 Hz, 6H); 2.97 ppm (h, $^3$J$_{HH}$=11 Hz, 1H); 7.39 ppm (d, $^3$J$_{HH}$=14.2 Hz, 2H); 7.47 ppm (h, $^3$J$_{HH}$=14.2 Hz, 2H); 7.49 ppm (s, 1H); 7.61 ppm (s broad, 34); 10.15 ppm (s broad, 3H).

The N-aryl-4,5-diaminopyrazoles described in the following Examples 3 to 9 can be prepared in a manner analogous to that of Examples 1 and 2 by using the corresponding hydrazines.

Example 3

1-(2-Methylphenyl)-4,5-diamino-1H-pyrazole
dihydrochloride $^1$H-NMR (DMSO-d$_6$): δ=2.06 ppm (s, 3H); 6.36 ppm (s broad, 3H); 7.26 ppm (d, $^3$J$_{HH}$=12.8 Hz, 1H); 7.25-7.40 ppm (m, 3H); 7.49 ppm (s, 1H); 10.09 ppm (s broad, 3H).

Example 4

1-(3-Methylphenyl)-4,5-diamino-1H-pyrazole
dihydrochloride $^1$H-NMR (DMSO-d$_6$): δ=2.38 ppm (s, 3H); 7.00 ppm (s broad, 3H); 7.21 ppm (d, $^3$J$_{HH}$=12.2 Hz, 1H); 7.30-7.45 ppm (m, 3H); 7.49 ppm (s, 1H); 10.14 ppm (s broad, 3H).

Example 5

1-(4-Methylphenyl)-4,5-diamino-1H-pyrazole
dihydrochloride $^1$H-NMR (DMSO-d$_6$): δ=2.37 ppm (s, 3H); 6.69 ppm (s broad, 3H); 7.32 ppm (d, $^3$J$_{HH}$=13 8 Hz, 2H); 7.43 ppm d, $^3$J$_{HH}$=13.8 Hz, 2H); 7.47 ppm (s, 1H); 10.12 ppm (s broad, 3H).

Example 6

1-(2,4-Methylphenyl)-4,5-diamino-1H-pyrazole
dihydrochloride $^1$H-NMR (DMSO-d$_6$): δ=1.99 ppm (s, 3H); 2.32 ppm (s, 3H); 4.49 ppm (s broad, 3H); 7.14 ppm (m centered, 2H); 7.22 ppm (s, if); 7.49 ppm (s, 1H); 10.04 ppm (s broad, 3H).

Example 7

1-(2,5-Methylphenyl)-4,5-diamino-1H-pyrazole
dihydrochloride $^1$H-NMR (DMSO-d$_6$): δ=2.00 ppm (s, 3H); 2.32 ppm (s, 3H); 4.49 ppm (s broad, 3H); 7.07 ppm (s, 1H); 7.10-7.30 ppm (m, 2H); 7.46 ppm (s, 1H); 10.11 ppm (s broad, 3H).

Example 8

4,5-Diamino-1-(2-ethylphenyl)-1H-pyrazole
dihydrochloride

Elemental analysis: C$_{11}$H$_{14}$N$_4$×2 HCl×0.5H$_2$O (mol. wt. =284.19)

|  | C | H | N | Cl |
| --- | --- | --- | --- | --- |
| Calculated: | 46.5% | 6.03% | 19.71% | 24.95% |
| Found: | 47.0% | 5.90% | 19.80% | 25.07% |

Example 9

1-(2-Pyridinyl)-4,5-diamino-1H-pyrazole dihydrochloride $^1$H-NMR (DMSO-d$_6$): δ=7.35 ppm (m, 1H); 7.57 ppm (s, 1H); 7.87 ppm (d, $^3J_{HH}$=12 Hz, 1H); 8.45 ppm (m, 1H); 10.04 ppm (s broad, 3H).

Elemental analysis: C$_8$H$_9$N$_5$×2 HCl (Mol. wt. =248.11)

|  | C | H | N | Cl |
| --- | --- | --- | --- | --- |
| Calculated: | 38.73% | 4.47% | 28.23% | 28.58% |
| Found: | 39.1% | 4.3% | 27.7% | 28.4% |

Example 10

1-(4-Chlorophenyl)-4,5-diamino-1H-pyrazole hemisulfate

Step 10.1: 5-Amino-1-(4-chlorophenyl)pyrazole 21.5 g (0.12 mol) of 4-chlorophenylhydrazine hydrochloride was suspended in 150 mL of methanol, 5 mL of concentrated hydrochloric acid was added, and the mixture was heated at reflux, which gave a clear, yellow-brown solution. To this solution was added dropwise 11.5 g (0.12 mol) of dimethylaminoacrylonitrile over a period of 30 minutes. After 1.5 h at reflux, most of the solvent was removed under vacuum. The remaining residue was taken up in 40 mL of dimethylformamide, and 9 mL of concentrated ammonia solution was added at room temperature. The resulting white precipitate was filtered off and discarded. The clear filtrate was used in Step 10.2 without further purification.

Step 10.2: 5-Amino-1-(4-chlorophenyl)-4-(4-sulfophenylazo)pyrazole 20.8 g (0.12 mol) of sulfanilic acid was diazotized and to the mixture was then added with continuing ice cooling 18.9 g (0.23 mol) of sodium acetate. The dimethylformamide solution from Step 10.1 was added dropwise over a period of 30 minutes. During the addition, the suspension changed color from gray to yellow-brown. The mixture was allowed to agitate an additional 2 h at 5° C. after which it was allowed to stand overnight at room temperature. The next day, the reaction product was filtered off, the moist filter cake was suspended in 350 mL of dimethylformamide and heated to about 80° C. Then, first 19.2 g (0.19 mol) of triethylamine and then 100 mL of water were added to dissolve the intermediate product. The clear solution was allowed to agitate in the presence of 3.5 g of activated carbon for about 15 minutes and was then filtered warm. The residue on the filter was washed with a small amount of water. To the still warm filtrate was then added 17.8 mL (0.21 mol) of concentrated hydrochloric acid, and the resulting yellow suspension was cooled to 0 to 5° C. The precipitated product was removed by suction filtration and washed with 15-mL portions of isopropanol. The residue was dried at 60° C. This gave 23.8 g (63% of the theoretical) of 5-amino-1-(4-chlorophenyl)-4-(4-sulfophenylazo)pyrazole. Melting point; 260° C. (decomp.).

Step 10.3; 1-(4-Chlorophenyl)-4,5-diamino-1H-pyrazole hemisulfate 20 g (52.9 mmol) of 5-amino-1-(4-chlorophenyl)-4-(4-sulfophenylazo)pyrazole from Step 10.2 in 200 mL of methanol and 20 mL of water was hydrogenated for 6 hours on 2 g of moist Raney nickel (water content: 50%) at 60° C. and at a hydrogen pressure of 2 bar. The catalyst was removed under a nitrogen atmosphere. Amberlyst A 26 ion exchanger (basic form; about 44 g=64 mmol) was then gradually added to the filtrate with agitation until no sulfanilic acid could be detected in the filtrate by thin-layer chromatography. The ion exchanger was filtered off and washed 4 times with 50-mL portions of methanol. The filtrate was introduced directly into a previously prepared solution of 3 g (30 mmol) of sulfuric acid and 20 mL of methanol, which caused the formation of a yellowish, coarsely crystalline precipitate. The precipitate was filtered off, washed with a small amount of Isopropanol and dried at 60° C. under vacuum. This gave 8.9 g (35 mmol, 65% of the theoretical) of crude product.

For purification, the 8.9 g (35 mmol) of crude product was dissolved in a mixture of 90 mL of isopropanol and 5 mL (40 mmol) of triethylamine. The clear, light-red filtrate was then allowed to agitate with 1 g of activated carbon at about 30° C. for about 15 minutes and was then filtered into a solution of 1 mL (20 mmol) of concentrated sulfuric acid and 100 mL of isopropanol. The resulting thick suspension was cooled in an ice bath, allowed to agitate for an additional 30 minutes and then filtered. The precipitate was washed with a small amount of isopropanol and dried at 60° C. under vacuum. Yield: 8.5 g (95.3% of the theoretical).

8.4 g (32 mmol) of the product thus obtained was dissolved in 40 mL of water and 2 mL of isopropanol by allowing the mixture to agitate for 30 min at room temperature. The solid was filtered off and washed first with a small amount of cold water and then several times with a total of 30 mL of isopropanol, until the washings became colorless. Drying at 60° C. under vacuum gave 7.63 g (91.28% of the theoretical) of 1-(4-chlorophenyl)-4,5-diamino-1H-pyrazole hemisulfate; melting point: 227.3° C. (decomp.).

$^1$H-NMR (DMSO-d$_6$): δ=6.90 ppm (s very broad, 6H); 7.32 ppm (s, 1H); 7.54 ppm (d, $^3J_{HH}$=14.8 Hz, 2H); 7.66 ppm (d, $^3J_{HH}$=14.8 Hz, 2H).

Elemental analysis: C$_9$H$_9$ClN$_4$×0.5H$_2$SO$_4$ (mol. wt.= 257.65)

|  | C | H | N | S | Cl |
| --- | --- | --- | --- | --- | --- |
| Calculated: | 41.96% | 3.91% | 21.75% | 6.22% | 13.75% |
| Found: | 42.08% | 3.64% | 21.80% | 6.14% | 13.65% |

Example 11

1-(4-Aminophenyl)-4,5-diamino-1H-pyrazole sulfate

Step 11.1: 5-Amino-1-(4-nitrophenyl)-1H-pyrazole 7.65 g (50 mmol) of 4-nitrophenylhydrazine was suspended in 70 mL of water and 10 mL of n-propanol and the suspension was heated to about 50° C. At this temperature, 5 g (50 mmol) of concentrated hydrochloric acid and 4.81 g (50 mmol) of 3-dimethylaminoacrylonitrile were then added. After an additional 15 minutes, 3.8 mL (50 mmol) of a 25% ammonia solution was added dropwise within 15 minutes. The reaction mixture was then allowed to agitate at about 50° C. until the 3-dimethylaminoacrylonitrile had completely reacted (about 1 hour) after which the resulting dark-brown suspension was cooled in an ice bath. The precipitate was filtered off, washed 3 times with small portions of cold water and then dried. Yield of crude product: 9.4 g (46 mmol. 92% of the theoretical).

The resulting crude product was used in Step 11.2 without further purification. A sample crystallized from 1:1 acetonitrile/water for analytical purposes had a melting point of 166.7° C.

Step 11.2: 5-Amino-1-(4-nitrophenyl)-4-(4-sulfophenylazo) pyrazole 7.79 g (45 mmol) of sulfanilic acid was diazotized, 7.38 g (90 mmol) of sodium acetate was added, and the reaction mixture was allowed to agitate at 0 to 5° C. for a about 15 more minutes. Then, 9.2 g (45 mmol) of 5-amino-1-(4-nitrophenyl)-1H-pyrazole from Step 11.1 (dissolved in 20 mL of dimethyl-formamide) was added dropwise over a period of 30 minutes. During the addition, the reaction mixture assumed a yellow-brown color, and an increasingly thick suspension formed. The suspension was diluted with about 50 mL of cold water, and the reaction mixture was allowed to stand overnight at room temperature. The precipitate was then removed by suction filtration and washed with a small amount of cold water. The moist, crude product thus obtained (about 14 g) was then suspended in 100 mL of isopropanol, 10 mL (72 mmol) of triethylamine was added, and the mixture was heated at reflux. After about 30 minutes, the reaction mixture was cooled slightly, and to it was added dropwise 14.5 mL (112 mmol) of a 25% hydrochloric acid solution which produced a thick, ocher-yellow suspension. The suspension was cooled to 0 to 5° C. and the precipitate was removed by suction filtration and washed with a small amount of ethyl acetate. The residue was dried at 60° C. under vacuum. This gave 12.18 g (31.4 mmol), 69.7% of the theoretical) of 5-amino-1-(4-nitrophenyl)-4-(4-sulfophenylazo)pyrazole; melting point: 135-136° C. (decomp.).

Step 11.3: 1-(4-Aminophenyl)-4,5-diaminopyrazole sulfate 11.65 g (30 mmol) of 5-amino-1-(4-nitrophenyl)-4-(4-sulfophenylazo)pyrazole from Step 11.2 was suspended in 140 mL of methanol and then hydrogenated on 0.3 g of Pd/C (10%) at 60° C. at a hydrogen pressure of about 2 bar. After approximately 1 hour, the reaction was complete, and the mixture was cooled to room temperature. The catalyst was filtered off under nitrogen, and the filtrate was allowed to agitate in the presence of 22.2 g (about 32 mmol) of Amberlyst A 26 ion exchanger (strongly basic) until sulfanilic acid could no longer be detected in the solution by chromatography. The ion exchanger was then filtered off under nitrogen and washed three times with three 30-mL portions of methanol. Immediately thereafter, the filtrate was added dropwise with agitation at room temperature to a mixture of 3.8 g (39 mmol) of concentrated sulfuric acid and 12 mL of methanol. The resulting suspension was suction-filtered and the solid was washed with a small amount of methanol and dried at 60° C. under vacuum. This gave 6.67 g (23.2 mmol, 77.4% of the theoretical) of crude product.

For purification, 1.30 g (4.5 mmol) of the crude product was suspended in 10 mL of isopropanol and 2.5 mL of water. After addition of 1.4 mL (10 mmol) of triethylamine and heating to about 35° C., the product dissolved and was allowed to agitate in the presence of 0.1 g of activated carbon for 15 minutes. The activated carbon was then removed by suction filtration, and to the solution was slowly added 0.3 mL (5.5 mmol) of concentrated sulfuric acid which caused formation of a reddish precipitate. The precipitate was filtered off, washed with a small amount of isopropanol and dried at 60° C. under vacuum. This gave 1.1 g (3.8 mmol, 85% of the theoretical) of 1-(4-aminophenyl-4,5-diaminopyrazole sulfate.

$^1$H-NMR (DMSO-d$_6$): δ=3.52 ppm (s very broad, 6H); 5.23 ppm (s very broad, 2H); 6.66 ppm (d, $^3J_{HH}$=14.4 Hz, 2H); 7.10 ppm (d, $^3J_{HH}$=14.4 Hz, 2H); 7.37 ppm (s, 1H).

Elemental analysis: $C_9H_{11}N_5 \times \frac{1}{2} H_2SO_4$ (mol. wt.= 257.69)

|  | C | H | N | S |
|---|---|---|---|---|
| Calculated: | 37.64% | 4.56% | 24.38% | 11.14% |
| Found: | 37.76% | 4.67% | 24.23% | 11.02% |

Example 12

Oxidative Hair Colorant, Basic

| | |
|---|---|
| 0.030 g | of ascorbic acid |
| 0.40 g | of sodium sulfite |
| 10.00 g | sodium lauryl ether sulfate, 28% aqueous solution |
| 7.85 g | of ethanol |
| X g | of pyrazole of formula (I) as per Table 1 |
| Y g | of coupler as per Table 1 |
| 9.10 g | of ammonia, 25% aqueous solution |
| to 100.00 g | demineralized water |

Just before use, 100 g of the above dye carrier composition was mixed with 100 g of a 6% aqueous hydrogen peroxide solution, and the required amount of the ready-for-use colorant solution was then applied to bleached hair. After an exposure time of 30 minutes at 40° C., the hair was washed with a shampoo, rinsed with water and dried. Table 1 summarizes the color shades obtained and the L*a*b* values.

TABLE 1

Dye Examples

| | | Coupler | | | |
|---|---|---|---|---|---|
| Developer | m-Aminophenol 0.27 g | Resorcinol 0.28 g | 5-Amino-2-methylphenol 0.31 g | 2,4-Diamino-1-(2'-hydroxy-ethoxy)benzol. 2HCl 0.60 g | N-(3-Dimethyl-aminophenyl)-urea 0.45 g |
| Pyrazole derivative of formula (I-a) 0.69 g | red L: 35.6 a: 40.33 b: 19.57 | strawberry L: 44.58 a: 35.58 b: 19.99 | orange L: 48.97 a: 42.41 b: 44.20 | red-violet L: 26.34 a: 39.80 b: 5.28 | steel-blue L: 28.15 a: 24.36 b: −25.58 |

TABLE 1-continued

Dye Examples

| Developer | Coupler | | | | |
|---|---|---|---|---|---|
| | m-Aminophenol 0.27 g | Resorcinol 0.28 g | 5-Amino-2-methylphenol 0.31 g | 2,4-Diamino-1-(2'-hydroxy-ethoxy)benzol. 2HCl 0.60 g | N-(3-Dimethyl-aminophenyl)-urea 0.45 g |
| Pyrazole derivative of formula (l-c) 0.69 g | red<br>L: 32.23<br>a: 37.59<br>b: 18.21 | pink-brown<br>L: 41.69<br>a: 33.21<br>b: 22.90 | orange<br>L: 47.96<br>a: 45.36<br>b: 46.95 | red-violet<br>L: 24.87<br>a: 38.59<br>b: 8.01 | dark-blue<br>L: 23.15<br>a: 18.94<br>b: −15.01 |
| Pyrazole derivative of formula (l-b) 0.69 g | red<br>L: 31.43<br>a: 38.78<br>b: 17.43 | pink-brown<br>L: 31.43<br>a: 38.78<br>b: 17.43 | orange<br>L: 48.51<br>a: 43.70<br>b: 46.04 | red-violet<br>L: 25.46<br>a: 37.80<br>b: 7.31 | steel-blue<br>L: 23.28<br>a: 18.97<br>b: −16.52 |
| Pyrazole derivative of formula (l-e) 0.69 g | red<br>L: 35.99<br>a: 41.85<br>b: 18.90 | pink-brown<br>L: 42.58<br>a: '33.68<br>b: 22.52 | orange<br>L: 50.50<br>a: 43.31<br>b: 45.38 | red-violet<br>L: 28.85<br>a: 40.77<br>b: 6.07 | steel-blue<br>L: 28.81<br>a: 25.84<br>b: −26.12 |
| Pyrazole derivative of formula (l-d) 0.69 g | red<br>L: 33.55<br>a: 41.38<br>b: 17.10 | strawberry<br>L: 44.77<br>a: 37.69<br>b: 20.17 | orange<br>L: 49.92<br>a: 43.29<br>b: 44.47 | red-violet<br>L: 27.16<br>a: 39.38<br>b: 4.38 | steel-blue<br>L: 26.14<br>a: 24.38<br>b: −24.96 |
| Pyrazole derivative of formula (l-g) 0.72 g | red<br>L: 34.08<br>a: 35.64<br>b: 17.46 | red-brown<br>L: 43.71<br>a: 30.44<br>b: 24.23 | bright orange<br>L: 48.99<br>a: 41.94<br>b: 46.00 | red-violet<br>L: 27.17<br>a: 36.49<br>b: 9.16 | dark blue<br>L: 27.39<br>a: 17.32<br>b: −13.58 |
| Pyrazole derivative of formula (l-f) 0.69 g | red<br>L: 36.28<br>a: 41.17<br>b: 21.53 | strawberry<br>L: 42.81<br>a: 36.66<br>b: 23.19 | bright orange<br>L: 51.56<br>a: 41.95<br>b: 46.56 | red-violet<br>L: 26.21<br>a: 39.29<br>b: 4.31 | steel-blue<br>L: 30.72<br>a: 23.82<br>b: −22.72 |
| Pyrazole derivative of formula (l-k) 0.64 g | red<br>L: 33.71<br>a: 32.59<br>b: 20.30 | deer-brown<br>L: 45.81<br>a: 27.99<br>b: 27.92 | orange-red<br>L: 49.06<br>a: 42.60<br>b: 47.77 | red-violet<br>L: 24.32<br>a: 35.11<br>b: 8.67 | blue<br>L: 26.97<br>a: 18.22<br>b: −12.63 |
| Pyrazole-derivative of formula (l-h) 0.69 g | red<br>L: 31.41<br>a: 39.10<br>b: 17.40 | red<br>L: 31.43<br>a: 38.78<br>b: 17.43 | bright orange<br>L: 46.01<br>a: 46.31<br>b: 45.91 | red-violet<br>L: 24.27<br>a: 37.34<br>b: 7.44 | blue<br>L: 22.77<br>a: 20.25<br>b: −16.41 |
| Pyrazole derivative of formula (l-i) 0.72 g | red<br>L: 30.05<br>a: 38.81<br>b: 18.26 | strawberry<br>L: 40.74<br>a: 35.42<br>b: 22.77 | brilliant orange<br>L: 43.46<br>a: 47.16<br>b: 42.63 | red-violet<br>L: 22.93<br>a: 33.51<br>b: 4.02 | dark blue<br>L: 23.60<br>a: 18.86<br>b: −19.96 |
| Pyrazole derivative of formula (l-l) 0.62 g | red<br>L: 26.91<br>a: 36.72<br>b: 14.74 | strawberry<br>L: 41.90<br>a: 32.58<br>b: 22.41 | brilliant orange<br>L: 39.40<br>a: 48.25<br>b: 37.40 | red-violet<br>L: 20.79<br>a: 28.40<br>b: 5.18 | dark blue<br>L: 22.87<br>a: 19.33<br>b: −13.53 |

In material reproduced from the original German document (Tables 1, 2), commas denote decimal points - Translator The L*a*b* color values given in the present example were determined with a Minolta Chromameter CR 300 color-measuring instrument. The L-value stands for brightness (namely the lower the L-value the higher is the color intensity), whereas the a-value is a measure of the red content (meaning that the higher the a-value, the higher is the red content). The b-value is a measure of the blue content of the color, namely the more negative the b-value the higher is the blue content.

Example 13

Oxidative Hair Colorant in Cream Form, Basic

| | |
|---|---|
| 15.00 g | of cetylstearyl alcohol (50/50) |
| 5.00 g | of glycerol monostearate |
| 2.00 g | of Cocamide DEA |
| 10.00 g | of sodium lauryl ether sulfate, 28% aqueous solution |
| 0.30 g | of ascorbic acid |
| 0.40 g | of sodium sulfite |
| X g | of dyes as per Table 2 |
| 4.50 g | of ammonia, 25% aqueous solution |
| to 100.00 g | demineralized water |

Just before use, 100 g of the above dye carrier composition (pH=10 to 10.5) was mixed with 100 g of a 6% aqueous hydrogen peroxide solution, and the required amount of the resulting ready-for-use oxidative hair colorant was applied to bleached hair. After an exposure of 30 minutes at 40° C., the hair was washed with a shampoo, rinsed with water and dried. Table 2 summarizes the shades obtained.

TABLE 2

| | Example | | |
|---|---|---|---|
| Dye | 13 a | 13 b | 13 c |
| 4,5-Diamino-1-(4'-methoxyphenyl)-pyrazole.2HCl | 1.43 g | | 0.62 g |
| 4,5-Diamino-1-{4'-isopropylphenyl}-pyrazole.2HCl | | 1.44 g | 0.65 g |
| 3-Aminophenol | | | 0.22 g |
| 4-Amino-3-methylphenol | 0.09 g | | 0.10 g |
| 5-Amino-2-methylphenol | 0.39 g | | 0.15 g |
| 3-Amino-2-chloro-6-methylphenol | 0.45 g | | 0.30 g |
| 1,3-Dihydroxybenzene | | 0.56 g | |
| 2-Amino-6-chloro-4-nitrophenol.HCl | 0.25 g | 0.51 g | |
| 2-Chloro-6-(ethylamino)-4-nitrophenol | | 0.05 g | 0.10 g |
| 1,4-Diamino-2-methylbenzene sulfate | | | 0.31 g |
| 1,4-Diamino-2-(2'-hydroxyethyl)-benzene sulfate | | | 0.20 g |
| N-(3-(Dimethylamino)phenyl)urea | | | 0.34 g |
| Shade obtained | brilliant cinder-red | brilliant red-gold | eggplant + red-violet reflections |

Example 14

Oxidative Hair Colorant in Gel Form

| | |
|---|---|
| 15.00 g | of oleic acid |
| 3.00 g | of glycerol |
| 7.00 g | of isopropanol |
| 0.50 g | of ascorbic acid |
| 0.40 g | of sodium sulfite |
| 0.40 g | of sodium hydroxide |
| 10.00 g | of ammonia, 25% aqueous solution |
| 0.90 g | of 1-(4-aminophenyl)-4,5-diamino-1H-pyrazole sulfate (1:1) |
| 0.31 g | of 1,4-diamino-2-methylbenzene sulfate |
| 0.20 g | of 1,4-diamino-2-(2-hydroxyethyl)benzene sulfate |
| 0.10 g | of 4-amino-3-methylphenol |
| 0.46 g | of 1,3-diamino-4-(2-hydroxyethoxy)benzene dihydrochloride |
| 0.33 g | of 5-[(2-hydroxyethyl)amino]-2-methylphenol |
| 0.21 g | of 3-aminophenol |
| to 100.00 g | demineralized water |

Just before use, 100 g of the above dye carrier composition (pH=10.8) was mixed with 100 g of a 6% aqueous hydrogen peroxide solution, and the required amount of the resulting ready-for-use oxidative hair colorant was applied to 50% gray human hair. After an exposure time of 30 minutes at 40° C., the hair was washed with a shampoo, rinsed with water and dried. The hair color was black with eggplant reflections.

Example 15

Oxidative Hair Colorant in Cream Form, Acidic

| | |
|---|---|
| 15.00 g | of cetylstearyl alcohol (50/50) |
| 5.00 g | of glycerol monostearate |
| 2.00 g | of Cocamide DEA |
| 10.00 g | of sodium lauryl ether sulfate, 28% aqueous solution |
| 0.30 g | of ascorbic acid |
| 0.40 g | of sodium sulfite |
| 1.00 g | of 4,5-diamino-1-(4-chlorophenyl)pyrazole hemisulfate |
| 0.25 g | of 5-[(2-hydroxyethyl)amino]-1,3-benzodioxol hydrochloride |
| 0.18 g | of 3-amino-2-chloro-6-methylphenol |
| 0.22 g | of 6-amino-3,4-dihydro-2H-1,4-benzoxazine dihydrochloride |
| to 100.00 g | demineralized water |

Just before use, 100 g of the above dye carrier composition (adjusted to pH=6.6 with 25% ammonia) was mixed with 100 g of a 6% aqueous hydrogen peroxide solution, and the required amount of the resulting ready-for-use oxidative hair colorant was applied to different kinds of hair. After an exposure time of 30 minutes at 40° C., the hair was washed with a shampoo gentle to colored hair, rinsed with water and dried. The following coloring results were obtained:

buffalo hair, bleached: egg-plant colors

50% gray human hair: egg-plant colors, gray parts fully covered medium-brown human hair: dark egg-plant colors.

Example 16

Oxidative Colorant

| | |
|---|---|
| 0.30 g | of ascorbic acid |
| 0.40 g | of sodium sulfite |
| 10.00 g | of sodium lauryl ether sulfate, 28% aqueous solution |
| 7.85 g | of ethanol |

-continued

| | |
|---|---|
| 0.72 g | of 1-(4-aminophenyl)-4,5-diamino-1H-pyrazole sulfate (1:1) |
| 0.31 g | of 5-amino-2-methylphenol |
| 9.10 g | of ammonia, 25% |
| to 100.00 g | demineralized water |

Just before use, 100 g of the above dye carrier composition was mixed with 100 g of a 6% aqueous hydrogen peroxide solution, and the required amount of the resulting ready-for-use oxidative hair colorant was applied to bleached buffalo hair corresponding to a more strongly damaged human hair. After an exposure time of 30 minutes at 40° C., the hair was washed with a shampoo, rinsed with water and dried. An orange-red coloration was obtained.

Example 17

Oxidative Hair Colorant

| | |
|---|---|
| 15.00 g | of cetylstearyl alcohol (50/50) |
| 5.00 g | of glycerol monostearate |
| 2.00 g | of Cocamide DEA |
| 10.00 g | of sodium lauryl ether sulfate, 28% aqueous solution |
| 0.30 g | of ascorbic acid |
| 0.40 g | of sodium sufite |
| 1.38 g | of 4,5-diamino-1-(4'-methoxyphenyl)pyrazole.2HCl |
| 0.63 g | of 5-amino-2-methylphenol |
| 4.50 g | of ammonia, 25% aqueous solution |
| to 100.00 g | demineralized water |

Just before use, 100 g of the above dye carrier composition was mixed with 100 g of a 6% aqueous hydrogen peroxide solution, and the required amount of the resulting ready-for-use oxidative hair colorant was applied to bleached buffalo hair corresponding to more strongly damaged human hair. After an exposure time of 30 minutes at 40° C., the hair was washed with a shampoo, rinsed with water and dried. A brick-red coloration was obtained.

Unless otherwise indicated, all percentages given in the present patent application are by weight.

The invention claimed is:

1. A N-aryl-4,5-diaminopyrazole of formula I, or a physiologically compatible salt thereof with an organic or inorganic acid:

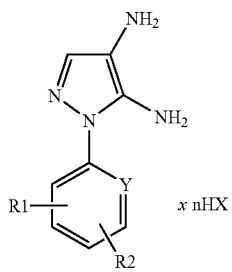

(I)

wherein R1 and R2, independently of each other, each denote a straight-chain or branched $C_1$–$C_6$-alkyl group, a hydroxyl group, a straight-chain or branched $C_1$–$C_6$-monohydroxyalkyl group, a straight-chain or branched $C_3$–$C_6$-dihydroxy-alkyl group, a straight-chain or branched $C_1$–$C_6$-alkoxy group, a straight-chain or branched $C_1$–$C_6$-hydroxyalkoxy group, a straight-chain or branched $C_3$–$C_6$-dihydroxyalkoxy group, an amino group, a $C_1$–$C_4$-monoalkylamino group, a di($C_1$–$C_4$)-alkylamino group, a $C_1$–$C_4$-aminoalkyl group, a halogen atom, a difluoromethyl group, or a trifluoromethyl group;

Y stands for a C—R3 group, wherein C is a carbon atom of the aryl group in the formula I and R3 is a hydrogen atom, a straight-chain or branched $C_2$–$C_6$-hydroxyalkoxy group, or a straight-chain, or branched $C_2$–$C_6$-alkoxyalkoxy group, or Y stands for a C—H group, R1 denotes a hydrogen atom and R2 denotes an amino group in position 4 of the aryl group of the formula I; and X denotes an acid radical and n has a value from 0 to 3.

2. The N-aryl-4,5-diaminopyrazole according to claim 1, wherein (i) R1 and R2, independently of each other, denote a methyl group, an ethyl group, an isopropyl group, said amino group, or a methoxy group, and Y stands for said C—H group; or (ii) Y stands for said C—H group and R1 denotes said hydrogen atom and R2 denotes said amino group.

3. The N-aryl-4,5-diaminopyrazole according to claim 1, wherein said salt is a sulfuric acid salt, a hydrochloric acid salt, a citric acid salt, or a tartaric acid salt.

4. The N-aryl-4,5-diaminopyrazole according to claim 1, wherein said salt is selected from the group consisting of 1-(2,4-dimethylphenyl)-4,5-diamino-1H-pyrazole dihydrochloride, 1-(2,5-dimethylphenyl)-4,5-diamino-1H-pyrazole dihydrochloride, and 1-(4-aminophenyl)-4,5-diamino-1H-pyrazole sulfate (1:1).

5. A colorant for oxidative dyeing of keratin fibers, said colorant containing at least one N-aryl-4,5-diaminopyrazole of formula (I), or a physiologically compatible salt thereof with an organic or inorganic acid:

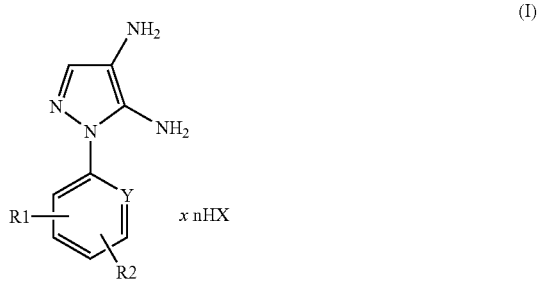

(I)

wherein R1 and R2, independently of each other, denote a straight-chain or branched $C_1$–$C_6$-alkyl group, a hydroxyl group, a straight-chain or branched $C_1$–$C_6$-monohydroxyalkyl group, a straight-chain or branched $C_3$–$C_6$-dihydroxyalkyl group, a straight-chain or branched $C_1$–$C_6$-alkoxy group, a straight-chain or branched $C_1$–$C_6$-hydroxyalkoxy group, a straight-chain or branched $C_3$–$C_6$-dihydroxyalkoxy group, an amino group, a $C_1$–$C_4$-monoalkylamino group, a di($C_1$–$C_4$)-alkylamino group, a $C_1$–$C_4$-aminoalkyl group, a halogen atom, a difluoromethyl group, or a trifluoromethyl group;

Y stands for a C—R3 group, wherein C is a carbon atom of the aryl group in the formula I and R3 is a hydrogen atom, a straight-chain or branched $C_2$–$C_6$-hydroxyalkoxy group or a straight-chain, or branched $C_2$–$C_6$-alkoxyalkoxy group, or Y stands for a C—H group, R1 denotes a hydrogen atom and R2 denotes an amino group in position 4 of the aryl group of the formula I; and X denotes an acid radical and n has a value from 0 to 3.

6. The colorant according to claim 5, containing from 0.005 to 20 weight percent of said at least one N-aryl-4,5-diaminopyrazole of the formula (I).

7. The colorant according to claim 5, containing additional dye components selected from the group consisting of developers, couplers, 4-(2,5-diaminobenzyl-amino)aniline, 3-(2,5-diaminobenzylamino)aniline, natural dyes, dyes identical to natural ones, and synthetic direct dyes.

8. A ready-to-apply dyeing mixture for oxidative dyeing of keratin fibers, said dyeing mixture comprising a mixture of a colorant composition for oxidative dyeing of keratin fibers with an oxidant in a weight ratio from 5:1 to 1:3;

wherein said colorant composition contains at least one N-aryl-4,5-diaminopyrazole of formula (I), or a physiologically compatible salt thereof with an organic or inorganic acid:

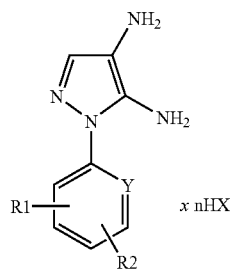

(I)

wherein R1 and R2, independently of each other, denote a straight-chain or branched $C_1$–$C_6$-alkyl group, a hydroxyl group, a straight-chain or branched $C_1$–$C_6$-monohydroxyalkyl group, a straight-chain or branched $C_3$–$C_6$-dihydroxyalkyl group, a straight-chain or branched $C_1$–$C_6$-alkoxy group, a straight-chain or branched $C_1$–$C_6$-hydroxyalkoxy group, a straight-chain or branched $C_3$–$C_6$-dihydroxyalkoxy group, an amino group, a $C_1$–$C_4$-monoalkylamino group, a di($C_1$–$C_4$)-alkylamino group, a $C_1$–$C_4$-aminoalkyl group, a halogen atom, a difluoromethyl group, or a trifluoromethyl group;

Y stands for a C-R3 group, wherein C is a carbon atom of the aryl group in the formula I and R3 is a hydrogen atom, a straight-chain or branched $C_2$–$C_6$-hydroxyalkoxy group or a straight-chain, or branched $C_2$–$C_6$-alkoxyalkoxy group, or Y stands for a C—H group, and R1 denotes a hydrogen atom and R2 denotes an amino group in position 4 of the aryl group in the formula I; and X denotes an acid radical and n has a value from 0 to 3.

9. The ready-to-apply dyeing mixture according to claim 8, wherein the ready-to-apply dyeing mixture has a pH of 3 to 11.

10. The ready-to-apply dyeing mixture according to claim 9, consisting of a hair colorant.

* * * * *